(12) United States Patent
Huang et al.

(10) Patent No.: US 7,750,208 B2
(45) Date of Patent: Jul. 6, 2010

(54) ANTHER-SPECIFIC EXPRESSION PROMOTER IN PLANT AND APPLICATION THEREOF

(75) Inventors: Pung-Ling Huang, Taipei (TW); Yi-Yin Do, Taipei (TW); Wei-Fen Huang, Taipei County (TW); Yi-Chun Liu, Taipei County (TW)

(73) Assignee: National Taiwan University, Taipei (TW)

( * ) Notice: Subject to any disclaimer, the term of this patent is extended or adjusted under 35 U.S.C. 154(b) by 83 days.

(21) Appl. No.: 12/170,346

(22) Filed: Jul. 9, 2008

(65) Prior Publication Data

US 2010/0011469 A1  Jan. 14, 2010

(51) Int. Cl.
C12N 15/82 (2006.01)
C12N 15/87 (2006.01)
A01H 1/00 (2006.01)
C12N 15/00 (2006.01)

(52) U.S. Cl. .................. 800/287; 800/278; 435/320.1

(58) Field of Classification Search ............... None
See application file for complete search history.

(56) References Cited

U.S. PATENT DOCUMENTS 5,477,002 A * 12/1995 Tuttle et al. .............. 800/303

OTHER PUBLICATIONS

Hamilton, et al.; "A Monocot Pollen-specific Promoter Contains Separable Pollen-specific and Quantitative Elements"; Plant Molecular Biology 38: 1998; pp. 663-669; Kluwer Academic Publishers; Netherlands.
Park, et al.; "BAN103, A Pollen-preferential Gene, from Chinese Cabbage and Its Promoter Activity"; Molecules and Cells, vol. 14, No. 1, 2002; pp. 150-157; Korea.
Okada, et al.; "Transcriptional Activity of Male Gamete-specific Histone gcH3 Promoter in Sperm Cells of *Lilium longiflorum*"; Plant and Cell Physiology 2005.
Lauri, et al.; "The Pollen-specific DEFH125 Promoter from Antirrhinum is Bound in Vivo by the MADS-box Proteins Desiciens and Globosa", Planta 2006 224; pp. 61-71.
Lang, et al.; "Functional Characterization of the Pollen-specific SBgLR Promoter from Potato (*Solanum Tuberosum L.*)"; Planta 2008 227; pp. 387-396.
Bate, et al.; "Functional Architecture of a Late Pollen Promoter: Pollen-specific Transcription is Developmentally Regulated by Multiple State-specific and Co-Dependent Activator Elements"; Plant Molecular Biology 37: 1998: pp. 859-869; Kluwer Academic Publishers; Belgium.
Garrido, et al.; "Promoter Activity of a Putative Pollen Monosaccharide Transporter in *Petunia hybrida* and Characterisation of a Transposon Insertion Mutant"; Protoplasma 2006 228; pp. 3-11; Austria.
Gupta, et al.; "Promoters of Two Anther-specific Genes Confer Organ-specific Gene Expression in a Stage-specific Manner in Transgenic Systems"; Plant Cell Rep; 2007; pp. 1919-1931; India.

* cited by examiner

*Primary Examiner*—Ashwin Mehta
*Assistant Examiner*—Li Zheng
(74) *Attorney, Agent, or Firm*—Schmeiser, Olsen & Watts LLP

(57) ABSTRACT

The invention provides an anther-specific expression promoter in plant, wherein said promoter is a promoter of Oncidium aureusidin synthase gene OgAS1, and has a sequence as SEQ ID No: 3. The invention provides further a gene expression cassette that comprised a promoter having a DNA sequence as SEQ ID No: 3, and a polynucleotide that encode an open reading frame and is linked to the 3' end of said promoter, wherein said promoter can activate the transcription of said polynucleotide in an organism containing said gene expression cassette. The invention provides also a gene expression vector that contains a promoter having DNA sequence as SEQ ID No: 3. The invention provides further a process for producing a transgenic plant or part of organ, tissue or cell of said transgenic plant containing the above-described gene expression cassette.

4 Claims, 5 Drawing Sheets
(2 of 5 Drawing Sheet(s) Filed in Color)

SEQUENCE LISTING

```
<160> NUMBER OF SEQ ID NOS: 9

<210> SEQ ID NO 1
<211> LENGTH: 1951
<212> TYPE: DNA
<213> ORGANISM: Antirrhinum majus
<220> FEATURE:
<221> NAME/KEY: CDS
<222> LOCATION: (96)...(1784)
<300> PUBLICATION INFORMATION:
<308> DATABASE ACCESSION NUMBER: Genbank/ AB044884
<309> DATABASE ENTRY DATE: 2008-02-19

<400> SEQUENCE: 1
aaattacatt gcttcctttg tcccaccttc caccaccaat atatacaact tcctcagcta      60
gttgtttatt atcaatcaaa taaaattatt tcccaatgtt caaaaatcct aatatccgct     120
atcacaaact atcttccaaa tccaatgaca acgatcaaga atcctcccat cgttgtaagc     180
acattctatt atttataata accttattcc tacttatagt tggcctgtac atcgccaact     240
ctctcgccta tgcccggttt gcctcgacct caaccggccc tatcgccgcc cctgatgtca     300
ccaaatgtgg tcagccagac ttgccacctg gcacagcccc aataaactgt tgtcccccaa     360
tccccgctaa aatcatcgat ttcgagctac cacctccctc cactaccatg agggttcgcc     420
gtgcggctca tttagttgat gatgcataca ttgccaaatt caagaaagcc gttgagctta     480
tgcgagctct acctgaggat gaccctcgta gcttcaagca acaagctaac gtccattgcg     540
cttactgcgc gggggcgtat aatcaagccg gtttcacaaa cctaaagctc caaatccacc     600
gatcttggct ttttttcccg ttccatagat attatatcta cttttttgaa agaatattgg     660
gaaaactaat caatgataca acttttgctc tcccattttg gaactatgat tcacctggtg     720
gaatgacaat cccatcaatg tttattgata ctaattcttc gctgtacgat agtttacggg     780
acagtaatca tcagccacca accatcgtag acttgaacta cgccttttct gattccgaca     840
ataccactac tcctgaagag caaatgatta taaaccttaa aattgtgtac agacaaatgg     900
tgtcgagcgc taagactcca cagcttttct tcggccgccc ataccgacgt ggggaccaag     960
agtttcccgg ggtgggggtcg attgagttag tccctcatgg catgatacat ttatggaccg    1020
gttctgagaa cacgccctat ggcgagaaca tgggggcttt ctactcaacg gctagagacc    1080
cgatattttt tgctcatcat tcgaacgtcg atagaatgtg gtccatatgg aagaccctag    1140
```

```
gagggccgcg gaggacggac ttaacagatc cagattttct tgatgcgtct ttcgtttttt    1200
atgacgaaaa cgcagagatg gttcgggtca aggttcggga ttgcttagat gaaaagaaac    1260
tagggtacgt ttatcaagat gtggagattc cgtggctcaa cactcgtcca acaccaaaag    1320
tttctccgtc tctacttaag aaatttcata gaacaaacac tgccaatccg agacaagttt    1380
ttcctgcgat acttgacaga gtcttaaaag ttatcgtgac gaggccgaag aaaactagaa    1440
gtaggaaaga aaaggacgag ttagaagaga ttttagtgat tgaagggatt gaactggaaa    1500
gagaccacgg gcacgtaaaa ttcgacgttt atattaatgc tgacgaagat gaccttgcgg    1560
tgatttcgcc ggagaatgct gagttcgccg ggagtttcgt gagtctgtgg cacaaaccta    1620
taaaggggaa gaggacaaag acgcagttat taacattgtc gatttgtgat attttggagg    1680
atttggatgc tgacgaagat gattatgtgt tggtcacttt ggttccgaga aacgccggag    1740
atgcgatcaa gattcataat gtcaagattg agcttgatgg ctaataaatt ctattgattt    1800
cttctcaacc tacagttgat catttaccga ttgattattc aataaaagt atctcatgta    1860 ccaatatcga tcgtattaat cgtaatactt tcagattttt atttatttaa aagcagttgt    1920
ataaatggtg aaataaggat tactttttga g                                    1951

<210> SEQ ID NO 2
<211> LENGTH: 1816
<212> TYPE: DNA
<213> ORGANISM: Oncidium Gower Ramsey

<400> SEQUENCE: 2
cccctccctt cctatgatca tcaatcaaga tgattcaaac tctttcctta ccaaagagat      60
tcctattgct cttctcccaa ttaccagctt ctccttgccc ccactactct cctctcctcc     120
tcctcctccc cctcctcttc ctagcttttc tcctcctctc gcctccacaa cctccccacc     180
gcccaatcca agcccgaat ctctccgaat gccaccccat ctttgtctca tcagcatcta     240
attcccctct tctcaactgc tgcccaccca tactctcccc gccttacaaa atcctcgact     300
tcacattccc tctcccaaac tcccctctcc gcacccgccg acccgctcac cttctcgact     360
cccactatat ttcccaatac tctaaagccg ttcagttaat gaaagatctc cccgacaccg     420
acccacgaag ttttaccag caggctaacg ttcactgcgc ttactgcaac ggcgcgtacg     480
accagcccgg tttctctaac ctccagcttc gcattcatgg gtcgtggttg tttttttccct    540 ggcacagatt ctatttatat ttccatgagc gcattctcgc caagcttatc ggggacgatt     600
cttttgctct tccttttggg aattgggacg aacccgctgg catgcaaatg ccttccgcgt     660
ttgtaaataa taattcttcc tcgctttatc atccgactag aaacccttcc cacttgccgc     720
cggtactagt ggatcttaat ttccatgaat tttggcttcg gaatcaaagt gatgagaatg     780
cccacagcgt agatgataat ctccggatca tgtacagaca gatgatacag aacggggcga     840
cctcggagct cttcatgggc tcagcaattc gtgccggaga tcatcccgaa cccggtggag     900
gttcggttga attcgttcca cacgacacgg ttcacacctg gaccggcgat ccacgtaacc     960
ataacgacga ggacatggga gctttctact cggccgcacg tgacccactt ttctacccac    1020
accacgcaaa catagatcgg ctctggtcgg tctggaaaac cctcggccca agcataagg     1080 acttctccga ctccgattgg ctcgactcaa cttttccactt ctacgacgag gaggcgcggc    1140
tcgttagagt gaagattaga gattgtattg atatggaccg attgcgatac cgttaccagg    1200
aagttgacaa tcagtggatc aatatgatcc atagaaccag gaagaagaag aagaaaagga    1260
```

| | |
|---|---|
| atattgggat aattaatatg agagaaaagg tgaagtttcc ggtgagcgtg gggaatgagg | 1320 |
| cggtggtggt gagtgtgaag aggccgaaga gaggtgggaa ggaggaagtg gaggttttgg | 1380 |
| tgatagaagg gatagagatt gatggaacgg attattcagt gaggtttgat gtgtatgtga | 1440 |
| atgcgtggcc agatgatttc aagcggccaa atgcgaggga atgtgcaggg agttttgtga | 1500 |
| gtttgccgcg gctgggaagg gtagtgaatg ggaggacgaa tttgaaattg gggataggtg | 1560 |
| agctgattga agaggaggag gattatgatg aagcagtgac ggtggcatta gtgccacgaa | 1620 |
| aaggaaaggc gactgtctct gccgtctata ttacatggct gtcgtgataa ttttaatgtg | 1680 |
| ccacaaattt ctatttattt gaagtgcaat gcatttcatt attacatggc tgtctaaatt | 1740 |
| acataagcat agcttttcat ataatagcta tgcttattat catcgttttc agaattgcat | 1800 |
| ttattatgag tttgct | 1816 |

<210> SEQ ID NO 3
<211> LENGTH: 3014
<212> TYPE: DNA
<213> ORGANISM: Oncidium Gower Ramsey

<400> SEQUENCE: 3

| | |
|---|---|
| gcattctagt gctctgaatg cttttaaaca gtttatgaac agtatatgaa tgattgggaa | 60 |
| caactctgtg gagtttctat tttgttataa ctgttgattt acagttttgc attttttgcta | 120 |
| aatagttgta gtttccttaa atgctgcatt taattgcact ggatcattaa atatgcatga | 180 |
| tgatgatagt ggctagccta ctaagggatt gatcatcccg ggatataccg tgttgcatgc | 240 |
| ccactgagat taacaaagct ataggcttgg ggtacttaga atttcagctc taagggtacg | 300 |
| ttggagccac gctccacggg ttttctcaga gatgtacact ctgtggttga gggcagatga | 360 |
| gcactggtat aaataataat gaaaggaatg aaatgaaatg cacggattga ttgtgaatgt | 420 |
| atgagcatat gattgggtac agtcttttga ctgggttttc agcttttagc ttctattgta | 480 |
| cagtctgttg actgggtgtt tttactttac gcttttacct gctttactgt ctttctgttt | 540 |
| cagtttggta gggtaggctg ggtagatgca gtctacctac tgggcttttt agctcatccc | 600 |
| ttttttcttgt acccttttgtt tctgtgcaga caagggtaaa aggccggcgg agtaggttcg | 660 |
| cggttcgatg agagcgtgga gcaggtggga cccttgagga taggtggttt tctttagcag | 720 |
| ttgtacattt ttgtactttt cttttaactg cttgtacacc tattctttg ttactatagc | 780 |
| tctggatgtt gttttgtttg tttctgatgt ttcgttcttt tcttttgatg ttgttttgtt | 840 |
| tgtttctgtt gtttcgttct tttcttttca cctccatagg ttgctgggca tgttttgcgc | 900 |
| gctcccgctc tgactcgact tgggtgcggg cccagaggag ggtgcaccgg gtcgggccgg | 960 |
| ggcggggtgc cacagtgttc atgtagctaa aaacatctta tgtggctcag atagagacta | 1020 |
| cttttcaaga agaaaggca atagaataca ctatcaattg tgatagatga aacatcatat | 1080 |
| tcgcctgcta cataaaaata tgatctcatc atggaagaaa tttgtgaagg tcaaaatcta | 1140 |
| gagagggatt tgactctaat tggtcatttt tttagctatt catcccatat atttattttt | 1200 |
| taacaatgat gaaaatcatg cttttctaaa gatctctaat taagtgtttg tttgtttcag | 1260 |
| cttcatggtg cggtgcttaa agtaaaagca tcgcaccgtc cgtttaacaa aaaaatagtt | 1320 |
| cttgtcgact caaatcgtag atacactagt gccgcttatc agcagctata gtaccgcttt | 1380 |
| tcactataga ggtgaagaga gagagagaga gagagagaga gagagagaga gagagagaga | 1440 |
| gagagagaga gagagagaga gaacaggaca tatataggcg aagatcggta ttcagtacat | 1500 |
| gaggtatcga catgttttac atgaagtatc gatatgtttt acatggagca ctgacctatt | 1560 |

```
ttaaatgaga taccgaccta ttttatatga agtatcgacc tattttggta ggtatcaacc    1620 cattttaca tgaaatatcg acctatttta catgaggtat tgacctttt acatgtgata    1680 ccaactattt atatgagata ctgatatatt tacatgaaat actgacatat tttagtaggt    1740
gtcggcctat gttgaaaggt gctgacatgt tttggtaggt accaacctat tttggtaagt    1800
gtcgaccggt tcccataggt aacagcatgt tttaatagat atagacctat tttttccata    1860
atgataatga taataataac aataataata ataataataa cattactatt aataatttta    1920
atattaataa aattaataat aataataatt taatagtgct aataaataata atattattaa    1980 tattaatgtt aataataata gtaataataa taatcataaa aattattatt attataataa    2040
taaacatctt ttcatacatc attttattaa aaaataatat ttatggcaca acagctacag    2100
taatatttct tccatccaaa taccacaaat atattttcat ttcttttcaa taaacagtag    2160
aaaacacttc ttccatattt tcttatcatt tgtttatgag ccgcttatta gcacaaccaa    2220
aacaaacgga tcctaaaagc tttctgattt ttaaaacttt attacttaag agggatgtgt    2280
atttcttcta tttaaagaat ataatttaca aattaattta aataattaaa ttttattata    2340
aaattaataa aatcaaacta atcaaattat ttttcaaata aaatcaaatt gaaataaact    2400
ttagttagtc aattgaataa tttgataata aatttaatta atatttaata tttataatat    2460
ataaattaag aagatttaca tacataccat ataattctaa tatatttaca tatctaacac    2520
tttaaaagtt ttacgttatc tttcaaatac gttcacctaa gcataagaat taatagtcat    2580 attttatat atgatgttaa aattccatgt tagattaaaa aataaaatta ggtgttgacc    2640
tagttgagac caattttcca tagtgctgaa ctagttgaga acaaaaaacg aaataccccta    2700 aaacaatgta tcactgctac atactacgta tatatcatga gatcgaactc tgcacacttg    2760
tacacaactc aataagtata cgactcaaat gcatttatta ttcacgatgt atataagcac    2820
ctctattaga actaattctg ttttatata accgttttct cttttatttg ttcattattt    2880
tgttttgctt caagctgtac ctataccggc tttctactgt atatatacct gtattctttc    2940
ttttttgtta taaaaattct aacagatgta aaccttcaac aacctcccct cccttcctat    3000
gatcatcaat caag                                                      3014
```

<210> SEQ ID NO 4
<211> LENGTH: 18
<212> TYPE: DNA
<213> ORGANISM: artificial sequence
<220> FEATURE:
<223> OTHER INFORMATION: forward primer

<400> SEQUENCE: 4
tgcatgcatg caagcttg                                                    18

<210> SEQ ID NO 5
<211> LENGTH: 37
<212> TYPE: DNA
<213> ORGANISM: artificial sequence
<220> FEATURE:
<223> OTHER INFORMATION: reverse primer

<400> SEQUENCE: 5
ataccatggc ccggggatcc tctagagtcg aggtcct                               37

<210> SEQ ID NO 6
<211> LENGTH: 21
<212> TYPE: DNA

```
<213> ORGANISM: artificial sequence
<220> FEATURE:
<223> OTHER INFORMATION: forward primer

<400> SEQUENCE: 6
ataccatggt acgtcctgta g                                             21

<210> SEQ ID NO 7
<211> LENGTH: 22
<212> TYPE: DNA
<213> ORGANISM: artificial sequence
<220> FEATURE:
<223> OTHER INFORMATION: reverse primer

<400> SEQUENCE: 7
acggccagtg ccaagcttgc at                                            22

<210> SEQ ID NO 8
<211> LENGTH: 21
<212> TYPE: DNA
<213> ORGANISM: artificial sequence
<220> FEATURE:
<223> OTHER INFORMATION: forward primer

<400> SEQUENCE: 8
gcattctagt gctctgaatg c                                             21

<210> SEQ ID NO 9
<211> LENGTH: 21
<212> TYPE: DNA
<213> ORGANISM: artificial sequence
<220> FEATURE:
<223> OTHER INFORMATION: reverse primer

<400> SEQUENCE: 9
acaccatggt gattgatgat c                                             21
```

ANTHER-SPECIFIC EXPRESSION PROMOTER IN PLANT AND APPLICATION THEREOF

BACKGROUND OF THE INVENTION

1. Field of the Invention

The invention relates to a tissue-specific gene promoter, and in particular, to a promoter useful for anther-specific expression in plant, and application thereof.

2. Description of the Prior Art

In the improvement of crop's characteristics, or in relative studies utilizing plant gene transfer technology, conventionally, a gene to be expressed or studied is constructed downstream of a specific promoter sequence and the gene to be studied is then expressed or modulated with the activation ability of said promoter. Among conventional techniques, over-expressing the target gene is mostly driven by the CaMV 35S promoter in plant. Unfortunately, CaMV 35S promoter is not a tissue-specific promoter in that it can not over-express a target gene at a specific plant tissue. Therefore, how to make over-expression of a target gene at a specific plant tissue or in a particular period is the key point to modulate a gene's expression.

Accordingly, for researches of bioscience or developments of the biotechnical industry, how to screen out promoters with different specificity to drive the expression of a transferred target gene at a target site and bring out a maximum benefit of gene transfer is the important topic for improving the development of biotechnical industry and increasing the economical benefit of crops.

At present, molecular biologists have found a number of promoters having spatial (i.e., specific cell or tissue) or temporal (i.e., at different growth and development stages) specificities, or promoters inducible by a specific substance such as UV-B or chemical substances, that can be used to activate the expression of a transferred target gene to achieve the purpose of modulating gene expression.

In genetic breeding, "heterosis" is a very important research trend for obtaining crop with better character. Heterosis is to be understood to mean that a first hybrid progeny (F1 progeny) generated from the hybridization of two parents has a character with average performance better than either parent. In the course of hybridization, if the crop of interest is a selfing crop, the parent should be subjected first to artificial castration and then pollination to increase in order to avoid selfing, which increases production cost. For example, in the breeding study of Cruciferae vegetables, selfing lineage of self incompatibility is currently used mostly to carry out F1 seed collection. Nevertheless, several bottlenecks such as instability of hybridization rate, difficulty in the propagation of selfing parent line, low seed collection due to selfing depression, as well as the unlikeliness for superior parent to have self incompatibility exist yet. To activate particular genes that may result in male sterility or ability to silence pollination-associated gene by means of an anther-specific promoter shall be an important contribution for improving character by applying biotechnology.

Though many studies have found promoters with anther- or pollen-specific activation activity, such as potato (Lang et al., 2008), tomato (Bate and Twell, 1998), maize (Hamilton et al., 1998), rice (Gupta et al., 2007), petunia (Garrido et al., 2006), antirrhinum (Lauri et al., 2006), lily (Okata et al. 2005), cabbage (Park et al., 2002) and the like, no study on gene promoter associated with an orchid has been reported so far. Oncidium Gower Ramsey is an important export cut flower for Taiwan. Its flower has a bright yellow color. Since customers desire visual aesthetic feeling and prefer novel flower colors, flower color becomes one of the important factors determining values in the flower crop industry and articles. In view of the foregoing, the inventors attempted to isolate genes associated with the biosynthesis of yellow pigment from Oncidium, and screened out promoters with tissue-specificity through the analysis of a promoter of aureusidin synthase gene.

Also, in view of the importance of developing promoters with distinct specificity for the biotechnology industry, the inventors had been devoted to improve and innovate, and, after intensive studying for many years, has developed successfully a anther-specific expression promoter in plant, and application thereof according to the invention.

SUMMARY OF THE INVENTION

One object of the invention is to provide a tissue-specific promoter useful for the specific expression in plant anther.

Another object of the invention is to provide an application of the anther-specific expression promoter in plant, wherein, by using the particular tissue-specificity of said promoter, there is overexpression of the target gene on the anther of plant.

Still another object of the invention is to provide a gene expression vector containing an anther-specific expression promoter that, through transferring a target gene via said vector into plant cell, overexpression of said gene can be done specifically on the anther of said plant under the control of said promoter.

As promoter useful for plant anther-specific expression to achieve the above-described objects of the invention, the source for the sequence of said promoter is the genomic DNA of Oncidium Gower Ramsey. To this end, a gene fragment of aureusidin synthase gene AmAS1 (GenBank accession number AB044884, SEQ ID No: 1) from Antirrhinum majus was used as a probe, a plaque hybridization reaction was carried out with Oncidium genomic DNA library. The resulting products were purified several times to obtain Oncidium aureusidin synthase genomic clone, which was then subjected to restriction map analysis and nucleic acid sequencing. After matching with cDNA sequence of Oncidium aureusidin synthase gene OgAS1 (SEQ ID No: 2), it could be confirmed that a local sequence of 3,014 bp (SEQ ID No: 3) at upstream of the translation start site (gene code: ATG) of Oncidium aureusidin synthase gene OgAS1, which comprised a promoter local sequence of 2,985 bp, and a 29 bp 5'-end untranslated region (5'UTR) in the first exon (exon 1) of Oncidium aureusidin synthase gene OgAS1. This 3,014 bp DNA sequence (SEQ ID No: 3) was used as Oncidium aureusidin synthase gene OgAS1 promoter.

In order to analyze whether said Oncidium aureusidin synthase gene OgAS1 promoter (SEQ ID No: 3) was tissue-specific, said promoter sequence was ligated to the 5'-end of the gene sequence of a reporter gene β-glucuronidase (GUS) to be used as the promoter for said reporter gene. The ligation product was then constructed into an *Agrobacterium tumefaciens* cloning vector to form a plasmid OgAS1p-GUS; then, by using *Agrobacterium tumefaciens* transfection, said OgAS1p-GUS plasmid was transferred into model plants *Arabidopsis thialana* and *Nicotiana tabacum* L., and the activity of said gene promoter was assayed by GUS histochemical staining. The result indicated that said Oncidium aureusidin synthase gene OgAS1 promoter (SEQ ID No: 3) could drive target gene to be expressed at the plant anther. Accordingly, the activation ability of Oncidium aureusidin synthase gene OgAS1 promoter (SEQ ID No: 3) according to the invention was extremely tissue-specific.

In addition to providing a promoter useful for plant anther tissue-specific expression, the invention also provides a gene expression cassette, said gene expression cassette consists of: (1) a promoter sequence (SEQ ID No: 3) according to the invention, and (2) a stretch of polynucleotide encoding an open reading frame (ORF), that is a target gene, wherein said polynucleotide is connected to the 3' end of the promoter according to the invention, and said promoter can activate the transcription of said polynucleotide in a organism containing said gene expression cassette. In a preferred embodiment, said target gene is a reporter gene β-glucuronidase (GUS).

Further, the Oncidium aureusidin synthase gene OgAS1 promoter (SEQ ID No: 3) according to the invention was constructed into a commercial gene cloning vector, including, but not limited to, pBI101, pBI121, pBIN19 (ClonTech), pCAMBIA1301, pCAMBIA1305, pGREEN (GenBank Accession No: AJ007829), pGREEN II (GenBank Accession No: EF590266), or pGreen0029 (John Innes Centre), to form a gene expression vector.

A target gene could be inserted in said gene expression vector such that said target gene was connected to the 3' end of the promoter according to the invention to form the above-described gene expression cassette. Through gene transferring, the promoter of the invention together with the target gene linked to its 3' end could be transferred into an objective plant, and further, the genomic constitution of the transgenic plant might be altered such that the promoter of the invention and said target gene could activate effectively the expression of said target gene in the objective transgenic plant and its progeny.

In another aspect, the invention provides a method for producing a transgenic plant or part of the organs of said transgenic plant.

In still another aspect, the invention provides a method for producing a tissue or cell containing the above-described gene expression cassette, said method comprising steps of:
   step 1: providing cells or tissue of an objective plant;
   step 2: transfecting a gene expression cassette containing promoter sequence (SEQ ID No: 3) of the invention into said cells or tissue of an objective plant obtained in step 2 to obtain a transfected cell or tissue of the plant; and
   step 3: cultivating said transfected cell or tissue of the plant obtained in step 2 to generate a transgenic plant or part of organs of said transgenic plant containing gene expression cassette encoding promoter sequence (SEQ ID No: 3) of the invention.

In step 2 of the above method, said transfection includes, but not limited to: Agrobacterium tumefaciens-mediation, gene recombination viral infection, transposon vector transformation, gene gun transformation, electroporation, microinjection, pollen tube transformation, liposome-mediated transformation, ultrasonic-mediated transformation, silicon carbide fiber-mediated transformation, electrophoresis, laser microbeam, polyethylene glycol (PEG), calcium phosphate transformation, DEAE-dextran transformation and the like.

These features and advantages of the present invention will be fully understood and appreciated from the following detailed description of the accompanying Drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is the result of Northern hybridization analysis for Oncidium.

FIG. 4 shows analytical results of the expression of reporter gene β-glucuronidase (GUS) at various tissue sites of the progeny from Arabidopsis thialana transformants containing OgAS1p::GUS-NOS gene expression cassette.

FIG. 5 shows analytical results of the expression for reporter gene β-glucuronidase (GUS) at various tissue sites in the progeny of Nicotiana tabacum L. transformant containing OgAS1p::GUS-NOS gene expression cassette.

DETAILED DESCRIPTION OF THE PREFERRED EMBODIMENT

Example 1

Northern Hybridization Analysis of Oncidium Aureusidin Synthase Gene

In order to reveal the expression site of Oncidium aureusidin synthase gene at Oncidium, RNA was extracted from various organs of Oncidium plant, and Northern hybridization analysis was carried out by using Oncidium aureusidin synthase gene OgAS1 (SEQ ID No: 2) as the probe.

1. Extraction of Oncidium RNA 5 g of Oncidium material was ground with liquid nitrogen in a mortar. To each gram of ground tissue was added 2-3 ml of sarcosyl-free solution D [4 M guanidiun thiocyanate, 25 mM sodium citrate (pH 7.0), 0.1 M β-mercaptoethanol], and equal volume of PCI (phenol: chloroform: isoamyl alcohol=25:24:1), and the resulting mixture was mixed homogeneously in a homogenizer. Additional sarcosyl was added to a final concentration of 0.5%. After being mixed further in homogenizer, the mixture was centrifuged at 4° C. 10,800 rpm for 20 minutes (Beckman J2-MC, JS 13.1). The supernatant was drawn and extracted with equal volume of PCI, followed with equal volume of CI (chloroform: isoamyl alcohol=49:1). The supernatant was subjected to extracting by adding 1/10 volume of 3 M NaOAc (pH 5.2) and 2.5-fold volume of −20° C. 100% ethanol, shaking homogeneously and left to precipitate at −80° C. overnight. On the next day, the mixture was centrifuged at 4° C. 10,800 rpm for 15 minutes. The pellet was washed with each of 2 mL of 70% and 100% ethanol, and then centrifuged at 4° C. 10,800 rpm for 5 minutes. The supernatant was discarded, and RNA was dissolved completely in water treated with diethyl pyrocarbonate (DEPC). To the solution, LiCl was added to a final concentration of 2.5M. Then, 1% β-mercaptoethanol was added, and the solution was allowed to precipitate at −80° C. overnight. On the next day, it was centrifuged at 4° C. 10,800 rpm for 90 minutes. The pellet was washed with 70% and 100% ethanol. RNA thus obtained was air-dried, and dissolved again for quantitative analysis.

2. Northern Hybridization Analysis of Oncidium Aureusidin Synthase Gene

Figures 1A, 1B:
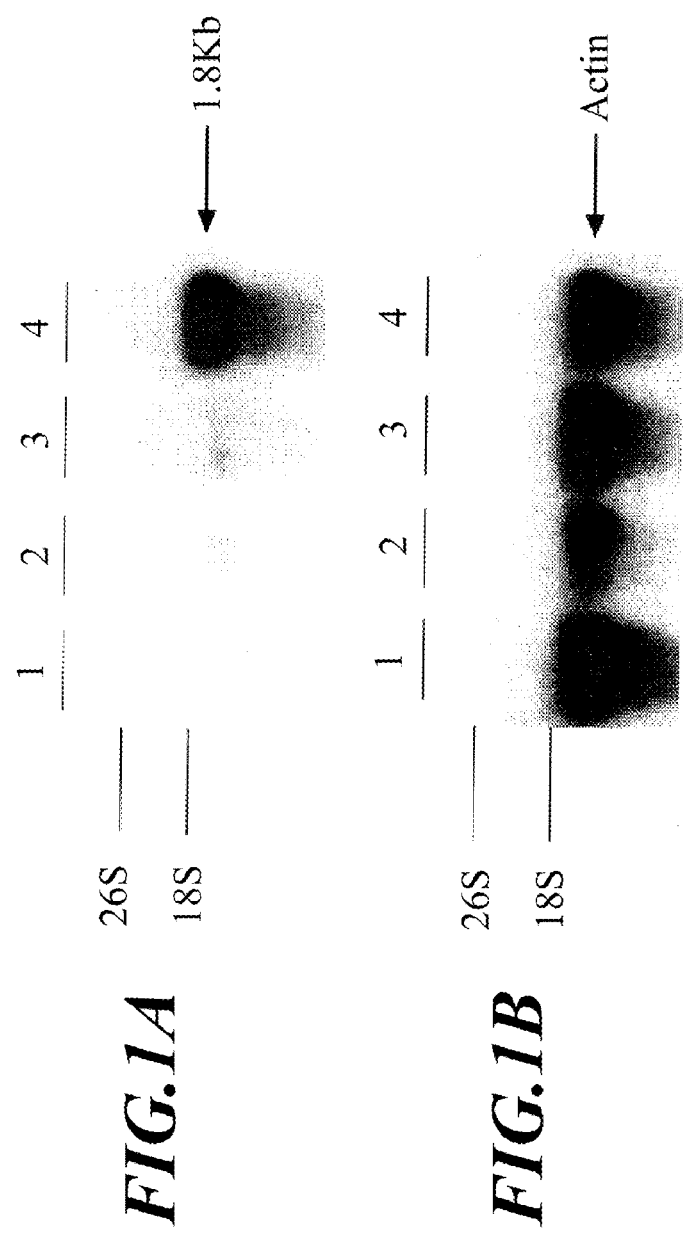
FIG. 1A shows the result of using Oncidium aureusidin synthase gene OgAS1 as the probe to analyze the expression of said gene in different sites of Oncidium plant.
FIG. 1B shows the result of using actin as the internal control; wherein lane 1: root; lane 2: pseudo-bulb; lane 3: leaf; lane 4: flower.

20 μg of total Oncidium RNA was glyoxylated at 50° C. for one hour, with a total reaction volume of 50 μL, comprising 10 mM sodium phosphate buffer (pH 7.0), 1 M deionized glyoxal, and 50% dimethyl sulfate. At the end of reaction, 10 μL 1×RNA loading buffer dye [containing 50% glycerol, 10 mM sodium phosphate (pH 7.0), 0.25% bromophenol blue] was added and electrophoresis was carried out on 1% agar gel. Then, the gel was treated with 50 mM sodium hydroxide for 30 minutes, and then with 200 mM sodium acetate for 30 minutes. The gel was then soaked in 1×TBE buffer [consisting of 90 mM Tris base, 2 mM EDTA (pH 8.0), and 89 mM boric acid] containing 1 μg/mL of ethidium bromide under shaking for 30 minutes. RNA loaded on the thus-treated gel was blotted on Hybond N membrane by capillary method. After 16-24 hours, its was treated with 5×SSPE at 65° C. for 5 minutes, and then dried in a vacuum oven at 80° C. for one hour. The membrane was transferred in a pre-hybridization solution (consisting of 5×SSPE, 5×BFP, 0.5% SDS, 50% formamide, 100 μg/mL salmon sperm DNA), and pre-hybridization reaction was carried out at 42° C. for more than 2 hours. Thereafter, the membrane was transferred in hybridization solution (consisting of 5×SSPE, 5×BFP, 0.5% SDS, 200 μg/mL salmon sperm DNA, 10% Dextran sulfate), where a hybridization reaction was performed at 65° C. for 16-18 hours. At the end of the reaction, it was washed twice with 2×SSPE and 0.1% SDS at room temperature for 15 minutes. The blotted membrane was then washed again with 1×SSPE and 0.1% SDS at 65° C. for 15 minutes. It was then subjected to exposure by pressing against an X-ray film. The result was shown in FIG. 1, and was indicated that the gene was expressed mainly at floral organ.

Example 2

Cloning of Oncidium Aureusidin Synthase Gene Promoter

1. Source of Oncidium λEMBL3 Genomic Library (Genomic Library)

Oncidium genomic library was constructed by extracting genome DNA from leaves of Oncidium Gower Ramsey, which, by using bacteriophage λEMBL3 as vector, and replacing DNA through enzymatic cleavage, was used to construct said genomic library.

2. Preparation of Nucleic Acid Probe and Labeling

A gene fragment of aureusidin synthase gene AmAS1 (GenBank accession number AB044884, SEQ ID No: 1) from Antirrhinum majus was used as a template to prepare a nucleic acid probe by means of Prime-A-Gene kit (Promega, USA) under following conditions: total reaction volume: 50 μL; reaction mixture consisting of 1× labeling buffer, pH6.6 {50 mM Tris-HCL, pH8.3, 5 mM $MgCl_2$, 2 mM DTT, 0.2 M HEPES [N-(2-hydroxyethyl)piperazine-N'-(2-ethanesulfonic acid)], 26$A_{260}$ unit/mL of random hexadeoxyribonicleotides}, 20 μM each of dATP, dGTP, dTTP, 500 ng/mL denatured DNA template, 400 μg/mL of Bovine serum albumin (BSA), 50 μCi [α-$^{32}$P] dCTP (333 nM), and 5 unit Klenow DNA Polymerase. After reacting at 37° C. for 2 hours, 2 μL 0.5 M EDTA (pH8.0) was added to terminate the reaction, followed by adding 8 μL of tracing dye (50% glycerol, 0.25% bromophenol blue). The reaction solution was passed through a Sephadex-G50 chromatograph column, eluted with TE buffer (pH7.6), and fractions of each 160~180 μL was collected in tubes. Each tube was counted in a liquid scintillation counter (Beckman 1801) to determine the radioactivity. Fractions with maximum radioactivity were used as the probe.

3. Selection of Oncidium Aureusidin Synthase Genomic Library

Plaque hybridization was used to select Oncidium genomic library. To this end, E. coli XL1-Blue MRA (P2) strain was used as the infection host for λEMBL3, and was cultivated in NZY medium (5 g/l of NaCl, 2 g/l of $MgSO_4$-$7H_2O$, 5 g/l of yeast extract). Selection was carried out under high stringency to obtain total of 150 million plaque forming units.

Next, bacteriophages were transferred on nitrocellulose membrane. The membrane was treated first with denaturing buffer (0.5 M NaOH, 1.5 M NaCl) for 2 minutes, and then treated with neutralization buffer [0.5 M Tris base, 1.5 M NaCl, 0.035% HCl (v/v)] for 5 minutes. Finally, it was soaked in 2×SSPE (1×SSPE, consisting of 0.18 M NaCl, 10 mM $NaH_2PO_4$, 1 mM EDTA pH7.4) for 30 seconds. It was placed in a vacuum oven at 80° C. for 2 hours to fix bacteriophage DNA. Thereafter, it was placed in a solution containing 2×SSPE and 0.1% SDS, and was shaken at room temperature for 1 hour. The nitrocellulose membrane thus treated was transferred in a pre-hybridization solution consisting of 5×SSPE, 5×BFP (1×BFP containing 0.02% BSA, 0.02% Ficoll-400000, 0.02% PVP-360000), 0.1% SDS, 50% formamide and 500 μg/mL of salmon sperm DNA, and a pre-hybridization reaction was carried out at 42° C. for 2 hours. A radio-labeled probe was used to carry out hybridization reaction with the membrane in 5×SSPE, 1×BFP, 0.1% SDS, 50% formamide and 100 μg/mL of salmon sperm DNA at 42° C. for 16~18 hours. Then, the nitrocellulose membrane was treated twice with wash buffer I (5×SSPE, 0.1% SDS) at room temperature for 15 minutes. Subsequently, the nitrocellulose membrane was further treated twice each with wash buffer II (1×SSPE, 0.5% SDS) at 37° C. for 15 minutes to wash off non-specific probe. After developing by exposure against X-ray film at −80° C. (Kodak XAR film), bacteriophage bearing target gene DNA could be detected. Said bacteriophage was isolated from medium and was stored in SM buffer containing 0.03% chloroform and was subjected to purification several times to obtain Oncidium aureusidin synthase gene OgAS1 genome clone λOgAS9.

4. DNA Extraction from λOgAS9 Bacteriophage Clone

Bacteriophage liquor of the above-described objective clone λOgAS9 was applied over NZY solid medium by scribing bacteriophage liquor with toothpick. 3 mL Top agar containing host cell E. coli XL1-Blue MRA (P2) was added and cultivated on the NZY solid medium at 37° C. for 8 hours. On the next day, a single plaque agar gel was dug from one line with a capillary and was cultivated further by spreading over NZY solid medium at 37° C. for 7~11 hours. Then, the culture medium was transferred to a refrigerator at 4° C., SM was added to release bacteriophages. The solution was collected in a centrifuge tube and chloroform was added thereto to 0.03%. The resulting mixture was centrifuged at 4° C. 7,000 rpm (Beckman J2-MC, JS-13.1) for 5 minutes, and then stored at 4° C. for use. Thereafter, large amount of the objective bacteriophage clone reproduced above was used to transfect host cells at a ratio of 5:1. To this, 1 mL SM buffer and 5 mL of 2.5 mM $CaCl_2$ was added and mixed, stored at room temperature for 15 minutes, and then at 37° C. for 45 minutes. It was then poured into 100 mL of 2×NZY liquid medium (0.4% MgSO₄☐7H₂O, 2% NaCl, 1% bacto-yeast extract, 2% NZ amine, 0.2% casaimino acid, 5 mM MgSO₄, 25 mM Tris-HCl pH7.5), and cultivated by shaking at 37° C. and 240 rpm for more than 8 hours. Thereafter, 4.5 mL chloroform was added thereto, and was treated by shaking at 37° C. and 240 rpm for 15 minutes, followed by centrifuged at 4° C. and 7,000 rpm for 20 minutes (Beckman J2-MC, JA 10 rotor). To its supernatant, 100 µL DNase I (1 mg/mL) and 100 µL RNaseA (10 mg/mL) were added, and the resulting mixture was treated at 37° C. and 80 rpm for 45 minutes. Next, 33 mL of 4 M NaCl was added, placed in an ice bath for 1 hour; followed by adding 33 mL of ice cold 50% polyethylene glycol, and settled at 4° C. overnight. The mixture was centrifuged at 4° C. and 5,000 rpm for 20 minutes (Beckman J2-MC, JA 10 rotor). The supernatant was discarded, and the pellet was air-dried. The solid precipitate was re-suspended in 500 µL PKB solution (10 mM NaCl, 10 mM Tris-HCl pH8.0, 10 mM EDTA, 0.1% SDS). To this suspension, proteinase K (final concentration 12.5 µg/mL) was added, and the resulting mixture was reacted at 37° C. for 20 minutes. The reaction mixture was then extracted successively with equal volume of phenol, PCI (phenol:chloroform:isoamyl alcohol=25:24:1), and CI (chloroform:isoamyl alcohol=24:1). The combined extract was centrifuged at room temperature and 14,000 rpm for 5 minutes. To the supernatant, 2-fold volume of −20° C. 100% ethanol was added, and the resulting mixture was centrifuged at 4° C. and 14,000 rpm for 10 minutes. The supernatant was decanted off, and the pellet was air-dried. The precipitated DNA was washed with 70% ethanol and 100% ethanol, respectively, dissolved in TE buffer (pH7.5), and stored at 4° C. for use.

5. Sequencing of DNA

An automatic nucleic acid sequencer ABI sequencer 377 was used to perform the sequencing of DNA, and thus determined the sequence of Oncidium aureusidin synthase genomic clone λOgAS9. It was analyzed with PC/Gene software available from IntelliGenetics Inc., and the result was shown in FIG. 2A. As shown, Oncidium aureusidin synthase genomic clone λOgAS9 had 2 exons, exon 1 and exon 2, with its translation start site (gene code: ATG) located at 30~32 nucleotides in exon 1, while the 3,014 bp local sequence of the promoter ahead of the transcription start site of the exon 1 (i.e. the first nucleic acid sequence on the exon 1) was as shown in SEQ ID No: 3.

Example 3

Figures 2A, 2B:
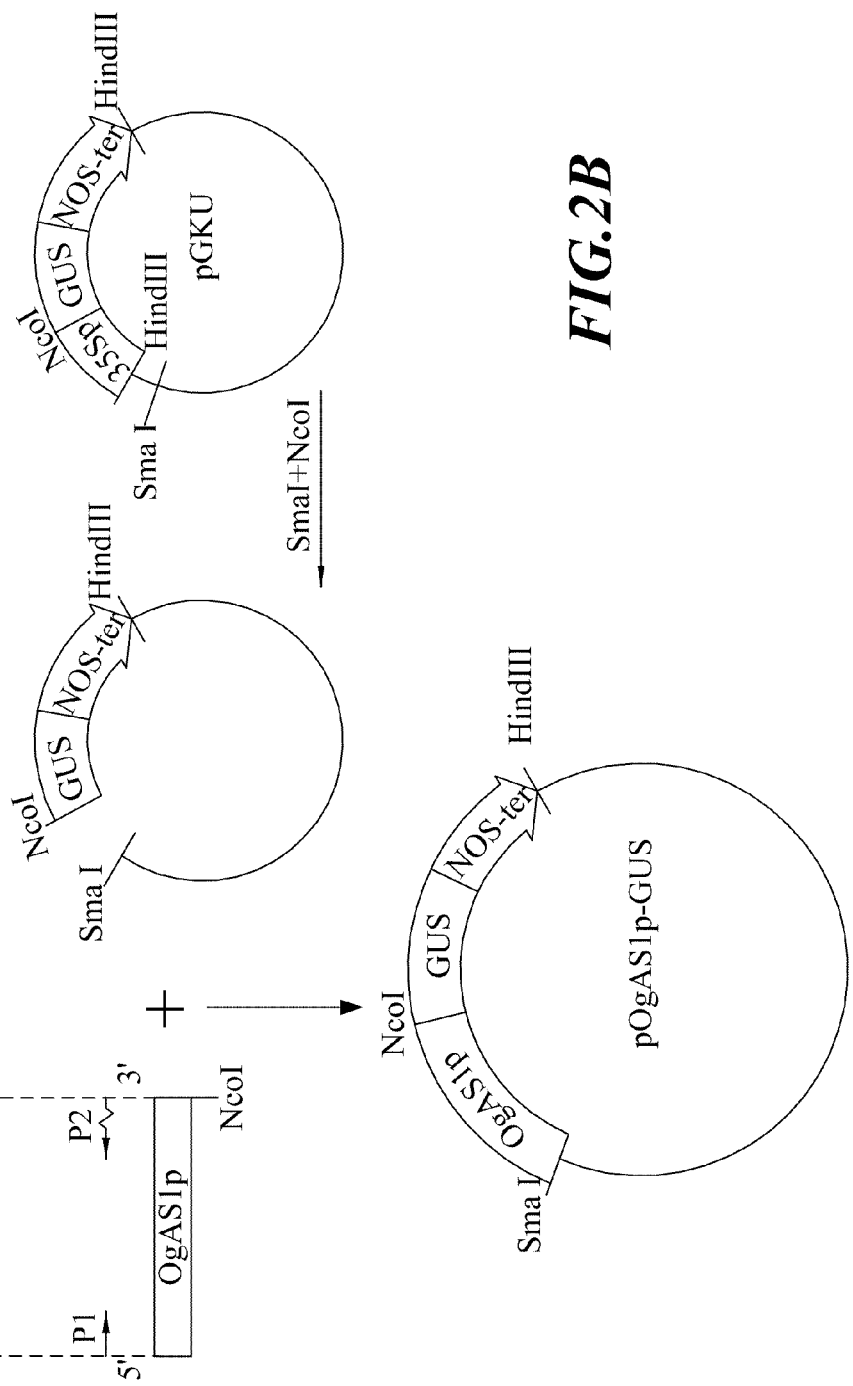
FIG. 2A is a restriction map of the genome of Oncidium aureusidin synthase gene OgAS1 according to the invention.
FIG. 2B shows the construction strategy for the plasmid OgAS1p-GUS containing the inventive Oncidium aureusidin synthase gene OgAS1 promoter.

Construction of a Vector Containing Oncidium Aureusidin Synthase Gene OgAS1 Promoter As shown in FIG. 2B, the construction strategy of Oncidium aureusidin synthase gene OgAS1 promoter comprised of constructing the 3,014 bp promoter sequence (SEQ ID No: 3) ahead of the translation start site of Oncidium aureusidin synthase gene OgAS1 into an Agrobacterium tumefaciens cloning vector pGKU to replace the original CaMV 35S promoter (35Sp) in a manner that the 3' end of the Oncidium aureusidin synthase gene OgAS1 promoter (SEQ ID No: 3) was linked to the 5' end of reporter gene β-glucuronidase (GUS) gene sequence, and used as the promoter of said reporter gene.

Step 1: Construction of Agrobacterium tumefaciens Cloning Vector pGKU

Figure 3:
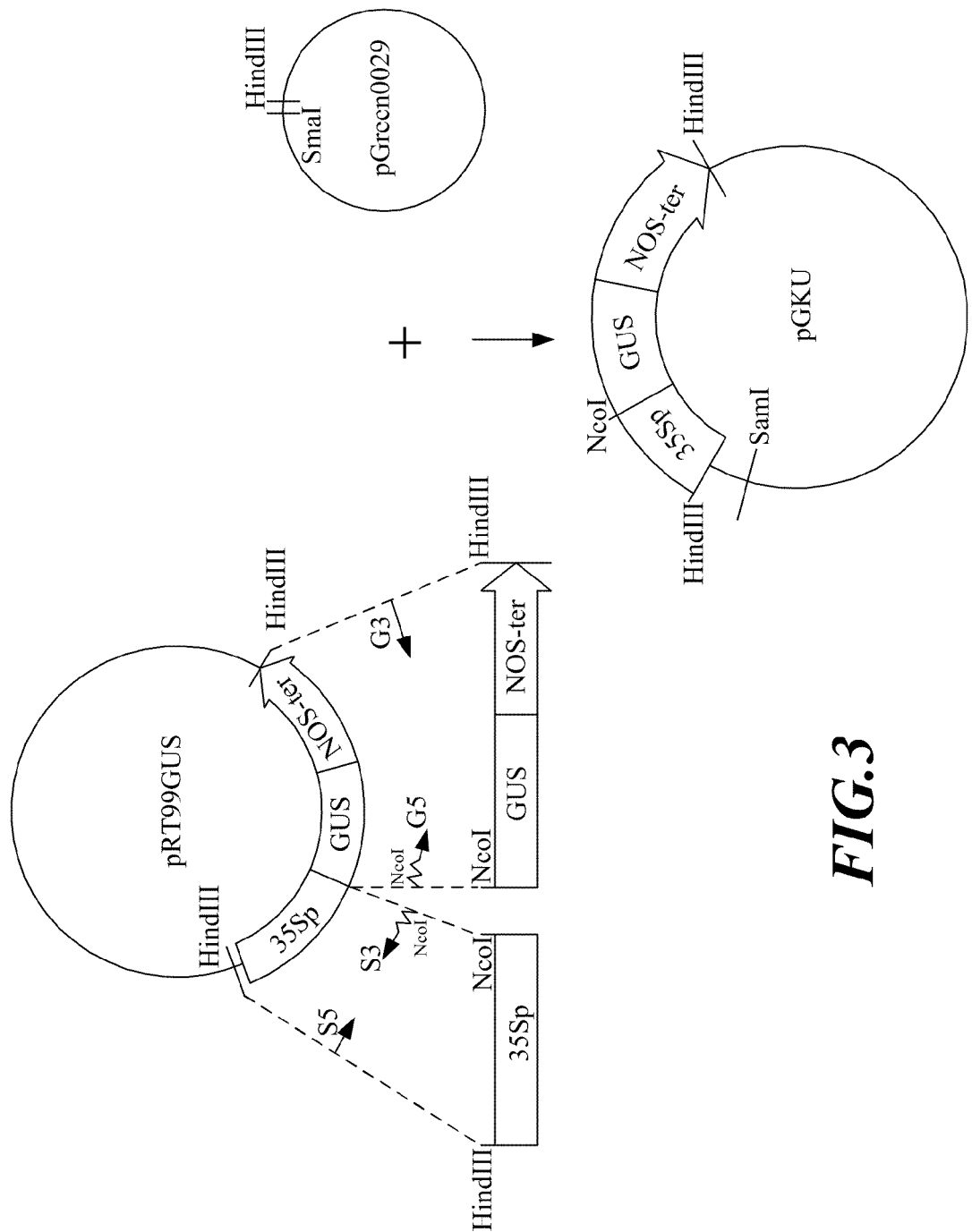
FIG. 3 is a construction strategy for Agrobacterium tumefaciens cloning vector pGKU.
Figure 4A:
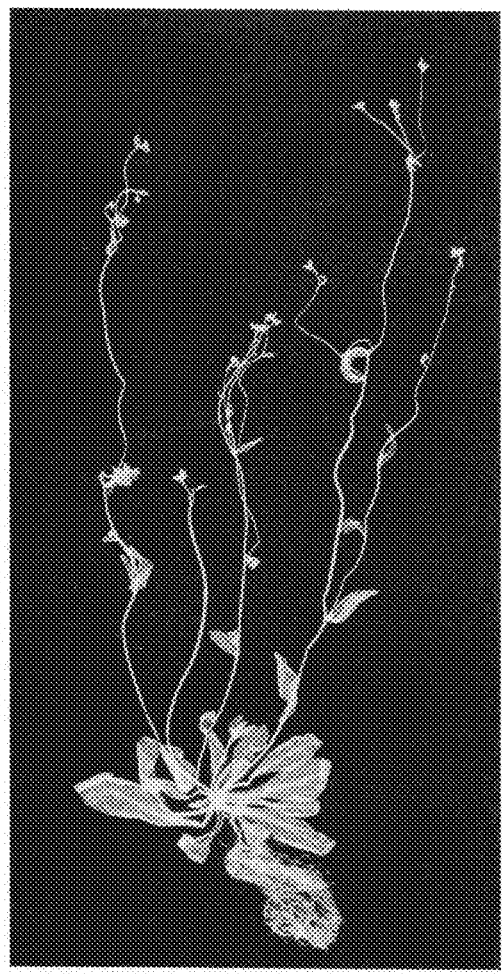
FIG. 4A: whole plant of 45-days old.
Figure 4B:
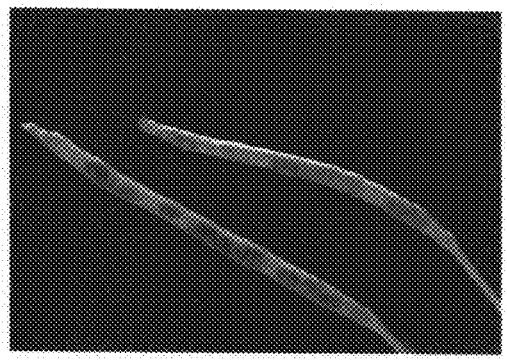
FIG. 4B: siliques of Arabidopsis thialana.
Figure 4C:
FIG. 4C: floral organ of Arabidopsis thialana.
Figure 4D:
FIG. 4D: floral organ of Arabidopsis thialana; all anther present blue color.

The construction strategy of Agrobacterium tumefaciens cloning vector pGKU was shown in FIG. 3. Briefly, a fragment of CaMV 35S promoter (35Sp)-reporter gene (GUS)-terminator (NOS-ter) (CaMV 35S::GUS-NOS) in a commercial vector pRT99GUS was constructed into a commercial Agrobacterium tumefaciens cloning vector pGreen0029 (John Innes Centre) to obtain Agrobacterium tumefaciens cloning vector pGKU. The construction strategy utilized polymerase chain reaction (PCR) to synthesize CaMV 35S promoter (35Sp) DNA fragment and reporter gene (GUS)-terminator (NOS-ter) DNA fragment, respectively, wherein, by means of the design of PCR primer, cleavage sites of NcoI restrictive enzyme were inserted at the 3' end of CaMV 35S promoter (35Sp) DNA fragment and the 5' end of reporter gene (GUS)-terminator (NOS-ter) DNA fragment, respectively. Finally, both PCR fragments were constructed into pGreen0029 to obtain Agrobacterium tumefaciens cloning vector pGKU.

Step 1.1: Obtaining CaMV 35S promoter (35Sp) fragment from commercial vector pRT99GUS DNA of commercial vector pRT99GUS was used as the template, and the amplification of the DNA sequence of CaMV 35S promoter (35Sp) fragment was carried out through PCR, wherein sequences of primers used in said PCR were as followed:

forward primer S5 (containing HindIII restrictive enzyme cleavage site):

```
                                    (SEQ ID No: 4)
5'-tgcatgcatgcaagcttg-3'
            HindIII
``` reverse primer S3 (containing NcoI restrictive enzyme cleavage site):

```
                                    (SEQ ID No: 5)
5'-ataccatggcccggggatcctctagagtcgaggtcct-3'
      NcoI
```

The total reaction volume of PCR was 50 µl (consisted of: 1 µl genome DNA, 10 µl 5× Phusion HF buffer, 1 µl 10 mM dNTP, 1 µl 20 of µM forward primer, 1 µl of 20 µM reverse primer, 35.5 µl of sterile water, 0.5 µl Phusion DNA polymerase) and PCR conditions were: 98° C. for 30 seconds, followed with total 35 cycles of 98° C. 10 seconds, 60° C. 30 seconds, and 72° C. 60 seconds, and finally 72° C. for 10 minutes as elongation. PCR product of 544 bp in length was synthesized. PCR product was digested with HindIII and NcoI restrictive enzymes, and DNA fragment (fragment S) of 470 bp in length was recovered and stored at 4° C. till used.

Step 1.2: Obtaining Reporter Gene (GUS)-Terminator (NOS-Ter) Fragment from Commercial Vector pRT99GUS Likewise, DNA of a commercial vector pRT99GUS was used as the template, and polymerase (PCR) was carried out to amplify DNA sequence of reporter gene (GUS)-terminator (NOS-ter) fragment, sequences of primers used in the PCR were as followed:

forward primer G5 (containing NcoI restrictive enzyme cleavage site):

```
                                    (SEQ ID No: 6)
5'-ataccatggtacgtcctgtag-3'
      NcoI
``` reverse primer G3 (containing HindIII restrictive enzyme cleavage site):

-continued (SEQ ID No: 7)
5'-acggccagtgccaagcttgcat-3'
            HindIII

Total reaction volume of PCR was 50 µl (consisted of: 1 µl genome DNA, 10 µl 5× Phusion HF buffer, 1 µl of 10 mM dNTP, 1 µl of 20 µM forward primer, 1 µl of 20 µM reverse primer, 35.5 µl of sterile water, 0.5 µl Phusion DNA polymerase). PCR conditions were: 98° C. for 30 seconds, followed with total 35 cycles of 98° C. 10 seconds, 60° C. 30 seconds, 72° C. 60 seconds, and finally, 72° C. for 10 minutes as elongation. PCR product of 2,108 bp in length was synthesized. The PCR product was digested with HindIII and NcoI restrictive enzymes, DNA fragment (fragment G) of 2,093 bp in length was recovered and stored at 4° C. till used.

Step 1.3: Ligation of DNA

A commercial vector pGreen0029 was digested with HindIII restrictive enzyme. DNA fragment (fragment P) of 4,632 bp in length was recovered. DNA ligation was carried out on fragment P together with fragment S (step 1.1) and fragment G (step 1.2) to obtain Agrobacterium tumefaciens cloning vector pGKU. As shown in FIG. 3, in Agrobacterium tumefaciens cloning vector pGKU, in addition to the character of pGreen, there were a CaMV 35S promoter (35Sp)-reporter gene (GUS)-terminator (NOS-ter) DNA fragment from commercial vector pRT99GUS, and an NcoI restrictive enzyme cleavage site at the 3' end of CaMV 35S promoter (35Sp). Accordingly, by means of the SmaI restrictive enzyme cleavage site in pGreen0029 as the multiple cloning site and NcoI restrictive enzyme cleavage site, Agrobacterium tumefaciens cloning vector pGKU could replace CaMV 35S promoter (35Sp) with other promoter sequence so as to activate reporter gene GUS.

Step 2: Obtaining Oncidium Aureusidin Synthase Gene OgAS1 Promoter (OgAS1p) Sequence Genomic DNA extracted from leaves of Oncidium Gower Ramsey plant in Example 2 was used as the template, polymerase chain reaction (PCR) was carried out to amplify the 3,014 bp sequence (SEQ ID No: 3) ahead the translation start site of Oncidium aureusidin synthase gene OgAS1, wherein, through the design of PCR primer, NcoI restrictive enzyme cleavage site was inserted at the 3' end of the fragment for subsequent construction.

Sequences of primers used in PCR were as followed:

forward primer P1:

5'-gcattctagtgctctgaatgc-3' (SEQ ID No: 8)

reverse primer P2 (containing externally added NcoI restrictive enzyme cleavage site):

(SEQ ID No: 9)
5'-acaccatggtgattgatgatc-3'
      NcoI

Total reaction volume of PCR was 50 µl (consisted of: 1 µl genome DNA, 10 µl 5× Phusion HF buffer, 1 µl of 10 mM dNTP, 1 µl of 20 µM forward primer, 1 µl of 20 µM reverse primer, 35.5 µl of sterile water, 0.5 µl Phusion DNA polymerase). PCR conditions were: 98° C. for 30 seconds, followed with 35 cycles of 98° C. 10 seconds, 65° C. 30 seconds, and 72° C. 60 seconds, and finally, 72° C. 10 minutes as elongation. PCR product was digested with NcoI, whole length DNA fragment was recovered and stored at 4° C. till used.

Step 3: Ligation of DNA

Agrobacterium tumefaciens cloning vector pGKU obtained in step 1 was subjected to double SmaI+NcoI restrictive enzyme digestion. pGKU vector thus digested was recovered, and was ligated with DNA fragment prepared in step 2 to obtain plasmid OgAS1p-GUS bearing Oncidium aureusidin synthase gene OgAS1 promoter sequence (SEQ ID No: 3). In said OgAS1-GUS plasmid, DNA sequence of reporter gene β-glucuronidase (GUS) was linked to the 3' end of Oncidium aureusidin synthase gene OgAS1 promoter (OgAS1p::GUS-NOS). Consequently, upon transformation of OgAS1-GUS plasmid in a plant body through Agrobacterium tumefaciens transformation, analysis on the mode for activating the gene expression of reporter gene β-glucuronidase (GUS) by Oncidium aureusidin synthase gene OgAS1 promoter could be studied.

Example 4

Transfection into Arabidopsis thialana Columbia Via Agrobacterium Tumefaciens-Mediated Process Model plant Arabidopsis thialana Columbia was used as the material, and plasmid OgAS1-GUS prepared in example 3 was transfected into Arabidopsis thialana Columbia by means of Agrobacterium tumefaciens inflorescence infiltration process in a manner that the genomic constitution in the transgenic plant could be altered. As a result, the Oncidium aureusidin synthase gene OgAS1 promoter could activate the expression of reporter gene GUS in the objective transgenic plant and progeny thereof. In addition, expression site of reporter gene GUS on Arabidopsis thialana Columbia transformant could be analyzed by GUS histochemical staining, and hence detected whether Oncidium aureusidin synthase gene OgAS1 promoter exhibited tissue-specificity.

1. Cultivation of Arabidopsis thialana Columbia Plant Material

Seeds of Arabidopsis thialana were wet and cold stratified at 4° C. for 2-4 days and sowed in a medium consisting of peat: Perlite: vermiculite in a ratio of 10:1:1. Cultivation conditions were: 22-25° C., 16 hours light cycle, and 75% relative humidity. After about 4-6 weeks, the plant was pruned. As the rachis had grown to a length of about 3 inches on 4-8 days after pruning, the plant was subjected to transformation.

2. Preparation of Agrobacterium tumefaciens Liquor and Infiltration

Agrobacterium tumefaciens LBA4404 strain was inoculated in YEB solid medium (0.5% beef extract, 0.1% yeast extract, 0.5% peptone, 0.5% mannitol, 0.05% $MgSO_4$, 1.25% agar, pH 7.5) containing suitable antibiotics (50 µg/ml of kanamycin, 50 µg/ml of ampicillin), and cultivated at 28° C. for 2 days. Then, single colony was picked and inoculated in 20 ml YEB liquid medium containing suitable antibiotics (50 µg/ml of kanamycin, 50 µg/ml of ampicillin) and cultivated by shaking at 28° C. and 240 rpm for 1 day. 5 ml bacteria liquor thus obtained was added in 200 ml YEB liquid medium and cultivated at 28° C. and 240 rpm for 9 hours. The culture suspension was centrifuged at 4° C. and 4,200 rpm for 20 minutes (Beckman J2-MC, JA-10 rotor). The supernatant was discarded, and the pellet was suspended in 20 ml pre-cooled YEB medium. The resulted suspension was centrifuged again at 4° C. and 4,200 rpm for 20 minutes. The pellet was re-suspended in 20 ml pre-cooled YEB medium and was stored at 4° C. till used. Agrobacterium tumefaciens transformation was performed employing frozen-thaw method. 500 µl suspension of *Agrobacterium tumefaciens* to be transformed was well mixed with 1 μg OgAS1p-GUS plasmid DNA prepared in Example 3, and the mixture was treated successively on ice, in liquid nitrogen and at 37° C., each for 5 minutes. The bacteria liquor was then mixed with 1 ml YEB medium and cultivated by shaking at 28° C. and 240 rpm for 3~4 hours. The bacterial liquor was applied over medium containing suitable antibiotics (50 μg/ml of kanamycin, 50 μg/ml of ampicillin), and cultivated at 28° C. for 2 days. *Agrobacterium tumefaciens* that had been transformed to contain plasmid OgAS1p-GUS prepared in example 3 was used to inoculate single colony of the above-described *Agrobacterium tumefaciens* on 5 ml YEB medium (0.5% beef extract, 0.1% yeast extract, 0.5% peptone, 0.5% mannitol, 0.05% MgSO$_4$, pH 7.5) containing suitable antibiotics (50 μg/ml of kanamycin, 50 μg/ml of ampicillin) and cultivated by shaking at 28° C. and 240 rpm for 2 days. Then, it was poured in 250 ml YEB medium containing suitable antibiotics (50 μg/ml of kanamycin, 50 μg/ml of ampicillin), and cultivated again by shaking at 28° C. and 240 rpm for more than 24 hours. It was then centrifuged at 4° C. and 6,000 rpm for 10 minutes. The supernatant was discarded, and the pellet was suspended in 200 ml infiltration medium (½ MS, 5% sucrose, 0.044 μM ABA, 200 μl/l or 0.01% Silwet L-77, pH 5.7). *Arabidopsis thialana* Columbia plants to be transformed were placed upside down in the *Agrobacterium tumefaciens* suspension, and soaked there for 20 seconds. *Arabidopsis thialana* Columbia plants were taken off and kept wet for 24 hours. Seeds could be harvested after about 3~4 weeks.

3. Sowing and Selection of Transformant

The transformed *Arabidopsis thialana* Columbia seeds thus-collected was rinsed several times with sterile water, treated with 70% ethanol for 2 minutes, treated with sterile water containing 1% Clorox and 0.1% Tween-20 for 20 minutes, and then rinsed 4-5 times with sterile water for 5 minutes each time. Thereafter, these seeds thus-treated were sown in germinating medium (½ MS, 1% sucrose, 0.7% agar, 50 μg/ml of kanamycin, 50 μg/ml of ampicillin) to carry out segregation assay of anti-antibiotic progeny. Homozygous transformant progeny thus obtained could be used in assay of promoter activity.

4. GUS Histochemical Staining

Tissue to be stained of the transformant was soaked first in pre-treatment buffer [50 mM Na$_3$PO$_4$ (pH6.8), 1% TritonX-100] at 37° C. for 2 hours, rinsed then 2~3 times with Triton X-100-free buffer (50 mM Na$_3$PO$_4$, pH6.8), and added thereto buffer (1 mM X-Gluc dissolved in 50 mM Na$_3$PO$_4$, pH6.8) containing X-Gluc (5-Bromo-4-chloro-3-indoxyl-beta-D-glucuronic acid). The mixture was evacuated at 25 inches-Hg for 5 minutes, returned to atmospheric pressure for 5 minutes, and this procedure was repeated once. Then, it was placed at 37° C. to react for 2 days. The enzymatic reaction and tissue discoloration were terminated with 70% ethanol, and the coloration status was observed under a microscope.

FIG. 4 shows the result of GUS activity analysis. As shown in FIG. 4, reporter gene GUS activated by Oncidium aureusidin synthase gene OgAS1 promoter could be expressed only at anther in *Arabidopsis thialana* Columbia transformant floral organ (FIGS. 4C and D), while no GUS activity could be detected in root, stem, leaf and pod of *Arabidopsis thialana* Columbia transformant (FIGS. 4A and B). Results from GUS activity analysis indicated that, Oncidium aureusidin synthase gene OgAS1 promoter exhibited characteristics to activate anther-specific expression, and significant activation ability.

Example 5

Transformation of *Nicotiana tabacum* L. Via *Agrobacterium tumefaciens*-Mediated Process Separately, *Nicotiana tabacum* L. cv Wisc. 38 was used as the material, and similarly, *Agrobacterium tumefaciens*-mediated transformation was employed to transform plasmid OgAS1p-GUS prepared in example 3 into *Nicotiana tabacum* L. to alter genomic constitution in the transgenic plant such that Oncidium aureusidin synthase gene OgAS1 promoter could activate effectively the expression of reporter gene GUS at objective transgenic plant and progeny thereof. Furthermore, GUS histochemical staining was used to analyze expression site of reporter gene GUS in *Nicotiana tabacum* L. transformant to detect whether Oncidium aureusidin synthase gene OgAS1 promoter exhibits likewise a tissue-specificity in *Nicotiana tabacum* L. plant.

1. Preparation of *Agrobacterium tumefaciens* liquor

The same procedure described in example 4 was followed in this example.

2. Transformation of *Agrobacterium tumefaciens*

The same procedure described in example 4 was followed in this example.

3. Small amount preparation of thus-transfected *Agrobacterium tumefaciens* plasmid The same procedure described in example 4 was followed in this example.

4. Transformation and selection of *Nicotiana tabacum* L.

Leaves of sterile seeding *Nicotiana tabacum* L. cv Wisc. 38 plants were cut into square of 1.5 cm×1.5 cm, placed on N01B1 solid medium (MS, adding 0.1 mg/L of 1-naphthyl acetic acid, 1 mg/L of BA, 3% sucrose, pH 5.7, 0.7% agar) and cultivated at 25° C., 16-hour lighting environment for 1 day. Then, the square leaves were dipped in bacterial liquor for 3-5 minutes. Next, they were placed on N01B1 solid medium, and cultivated at 25° C., 16-hour lighting environment for 3 days. Thereafter, those square leaves were soaked and washed in 20 mL N01B1 liquid medium containing 250 mg/L of cefotaxime for 1 minute. Subsequently, they were transferred on N01B1 solid medium containing 250 mg/L of cefotaxime and 100 mg/L of kanamycin, and were selected at 25° C., 16-hour lighting environment for about 3 weeks. Upon germination of adventitious buds from square leaves, those leaves were moved onto N01B1 solid medium containing 250 mg/l of cefotaxime and 200 mg/l of kanamycin. Selection was carried out at 25° C., 16-hour lighting environment. As shoots had grown to longer than 1 cm, shoots without etiolation could be cut and cottage cultivated in MS solid medium containing 250 mg/L of cefotaxime and 200 mg/L of kanamycin at 25° C. and 16-hour lighting environment till rooting. The plants were used in GUS activity assay.

5. Gus Histochemical Staining

The *Nicotiana tabacum* L. transformant survived in the above selection was subjected to GUS histochemical staining analysis followed the procedure described in example 4.

Figure 5A:
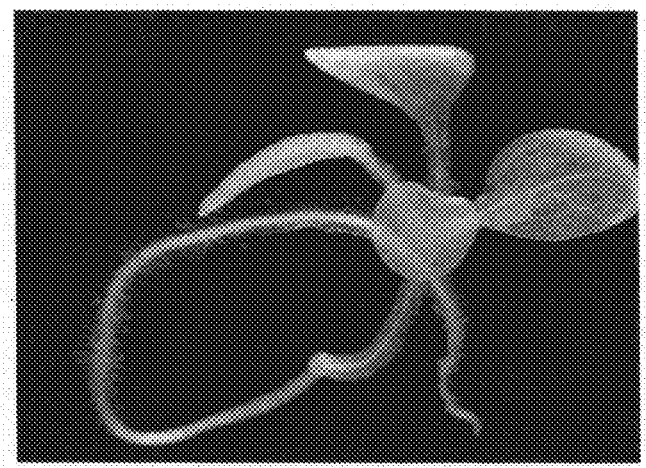
FIG. 5A: whole seedling at vegetative growth stage.
Figure 5B:
FIG. 5B: floral organ of Nicotiana tabacum L., only anther presenting blue color.
Figure 5C:
FIG. 5C: the pistil and stamen of Nicotiana tabacum L.

Results of GUS activity analysis shown in FIG. 5 indicated that reporter gene GUS activated by Oncidium aureusidin synthase gene OgAS1 promoter could be expressed only at anther of floral organ in *Nicotiana tabacum* L. transformant (FIGS. 5B and C); while *Nicotiana tabacum* L. seedlings at vegetative growth stage could not take place GUS coloration (FIG. 5A). Therefore, GUS activity analytical results from both of *Arabidopsis thialana* Columbia and *Nicotiana tabacum* L. transformants indicated that, Oncidium aureusidin synthase gene OgAS1 promoter could exhibit significant anther-specific activation ability in different species.

In summary, anther-specific promoter and application thereof provided according to the invention gives following advantages over other conventional techniques:

1. The promoter of the invention can activate the expression of gene behind its 3' end to express in anther, and by means of this particular tissue-specificity of said promoter, over-expressing target gene at anther of a plant.

2. The promoter of the invention can be transferred into a plant through a form of vector, and enables the over-expression of the target gene to take place in anther of the transgenic plant and progeny thereof. As the result, a vector containing the promoter of the invention can be used as a tool to modulate gene expression, which provides great value on industrial application.

While the detailed description provided above is directed to a possible embodiment of invention, it should be understood that said embodiment is not construed to limit the scope of the invention as defined in the appended claims, and those embodiments or alteration that can be made without departing from the spirit and scope of the invention are intended to fall within the scope of the appended claims.

Accordingly, the invention has indeed not only an innovation on the species gene, but also has particularly an expression uniqueness, and therefore, the application should meet sufficiently requirement of patentability on novelty and non-obviousness, and should deserve an invention patent right.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A anther-specific expression promoter in plant, said promoter comprising a nucleotide sequence having anther specific promoter activity consisting essentially of SEQ ID NO: 3.

2. A gene expression cassette, comprising:
   a promoter as defined in claim 1; and
   a polynucleotide encoding an open reading frame;
   wherein said polynucleotide is linked to the 3' end of said promoter, and said promoter can activate transcription of said polynucleotide in an organism containing said gene expression cassette.

3. A gene expression vector, comprising a promoter domain as defined in claim 1.

4. A plant or part of organ, tissue or cell of said plant containing via transformation a gene expression cassette as defined in claim 2.

* * * * *